(12) United States Patent
Vice

(10) Patent No.: US 9,872,650 B2
(45) Date of Patent: Jan. 23, 2018

(54) ELECTRODERMAL INTERFACE SYSTEM

(71) Applicant: Anthrotronix, Inc., Silver Spring, MD (US)

(72) Inventor: Jack M. Vice, Orlando, FL (US)

(73) Assignee: Anthrotronix, Inc., Silver Spring, MD (US)

( * ) Notice: Subject to any disclaimer, the term of this patent is extended or adjusted under 35 U.S.C. 154(b) by 0 days.

(21) Appl. No.: 14/716,084

(22) Filed: May 19, 2015

(65) Prior Publication Data

US 2015/0327808 A1 Nov. 19, 2015

Related U.S. Application Data

(60) Provisional application No. 62/000,489, filed on May 19, 2014.

(51) Int. Cl.
*A61B 5/0408* (2006.01)
*A61B 5/0492* (2006.01)
(Continued)

(52) U.S. Cl.
CPC .......... *A61B 5/6804* (2013.01); *A61B 5/0022* (2013.01); *A61B 5/02405* (2013.01); *A61B 5/04085* (2013.01); *A61B 5/0488* (2013.01); *A61B 5/0492* (2013.01); *A61B 5/7203* (2013.01); *A61B 5/7455* (2013.01); *A61N 1/0452* (2013.01); *A61N 1/36014* (2013.01);
(Continued)

(58) Field of Classification Search
USPC ................................................. 600/388–389
See application file for complete search history.

(56) References Cited

U.S. PATENT DOCUMENTS 5,549,656 A 8/1996 Reiss
5,607,454 A * 3/1997 Cameron ............. A61N 1/3937
607/5

(Continued)

OTHER PUBLICATIONS

Peckham, PH; "Functional Electrical Stimulation: Current Status and Future Prospects of Applications to the Neuromuscular System in Spinal Cord Injury" Paraplegia 25; pp. 279-288 (1987).*

*Primary Examiner* — Lee S Cohen
*Assistant Examiner* — Erin M Cardinal
(74) *Attorney, Agent, or Firm* — Lieberman & Brandsdorfer, LLC

(57) ABSTRACT

A communication system, method, and computer program product supported by electro-dermal monitoring physiological signals at the surface of the skin. The system includes a garment comprising an electro-dermal interface. The interface includes two or more electrodes in an array of electrodes. The electrodes are associated with three or more polarities. Two or more measurement circuits associated with respective measurement functions are in communication with the electrodes, including a first measurement circuit associated with a first measurement function and a second measurement circuit associated with a second measurement function. Switching circuitry comprising two or more pole switches, with each switch in communication with a respective electrode. A controller is in communication with the switching circuitry to change a measurement function. Changing the measurement function includes changing a polarity associated with at least one of the electrodes.

21 Claims, 9 Drawing Sheets

(51) Int. Cl.
*A61N 1/04* (2006.01)
*A61B 5/00* (2006.01)
*A61B 5/024* (2006.01)
*A61B 5/0488* (2006.01)
*A61N 1/32* (2006.01)
*A61N 1/36* (2006.01)

(52) U.S. Cl.
CPC ............. *A61B 5/024* (2013.01); *A61B 5/0408* (2013.01); *A61N 1/0484* (2013.01); *A61N 1/321* (2013.01); *A61N 1/36003* (2013.01)

(56) References Cited

U.S. PATENT DOCUMENTS

| | | | |
|---|---|---|---|
| 8,948,838 B2 * | 2/2015 | Goldkuhl | A61B 5/0531 600/382 |
| 2003/0032989 A1 * | 2/2003 | Herleikson | A61B 5/0531 607/8 |
| 2003/0088167 A1 * | 5/2003 | Fendrock | A61B 5/0408 600/372 |
| 2003/0233129 A1 * | 12/2003 | Matos | A61B 5/0006 607/5 |
| 2004/0242989 A1 * | 12/2004 | Zhu | A61B 5/0536 600/407 |
| 2005/0171534 A1 | 8/2005 | Habib | |
| 2006/0173510 A1 * | 8/2006 | Besio | A61B 5/0482 607/45 |
| 2007/0293918 A1 * | 12/2007 | Thompson | A61N 1/36021 607/72 |
| 2008/0046015 A1 * | 2/2008 | Freeman | A61H 31/005 607/6 |
| 2009/0240131 A1 * | 9/2009 | Lu | A61B 5/0028 600/372 |
| 2010/0079156 A1 * | 4/2010 | Lee, II | A61B 5/04001 324/692 |
| 2010/0145179 A1 * | 6/2010 | Lin | A61B 5/04 600/393 |
| 2011/0092790 A1 * | 4/2011 | Wilder-Smith | A61B 5/01 600/388 |
| 2011/0144634 A1 | 6/2011 | Rittman, III | |
| 2011/0282180 A1 * | 11/2011 | Goldkuhl | A61B 5/0531 600/393 |
| 2012/0016446 A1 * | 1/2012 | Panting | A61N 1/0484 607/62 |
| 2012/0065538 A1 | 3/2012 | Friedman | |
| 2012/0143028 A1 * | 6/2012 | Park | A61B 5/04 600/372 |
| 2012/0150011 A1 * | 6/2012 | Besio | A61B 5/04004 600/388 |
| 2012/0246795 A1 * | 10/2012 | Scheffler | A41D 1/002 2/69 |
| 2012/0254934 A1 * | 10/2012 | McBrearty | G06F 19/3481 725/118 |
| 2013/0281759 A1 | 10/2013 | Hagedorn et al. | |
| 2013/0337974 A1 * | 12/2013 | Yanev | G06F 19/3481 482/8 |
| 2014/0039571 A1 * | 2/2014 | Wolpaw | A61N 1/36082 607/45 |
| 2014/0336473 A1 * | 11/2014 | Greco | A61B 5/486 600/301 |
| 2014/0364703 A1 * | 12/2014 | Kim | A61B 5/0492 600/301 |

* cited by examiner

ELECTRODERMAL INTERFACE SYSTEM

CROSS REFERENCE TO RELATED APPLICATION(S)

This application is a non-provisional patent application claiming the benefit of the filing date of U.S. Provisional Patent Application Ser. No. 62/000,489, filed May 19, 2014, and titled "Electrodermal Interface System" which is hereby incorporated by reference.

BACKGROUND

The present embodiment(s) relates to a communication system that both measures human physiology and conveys messages through the skin of the user. More specifically, the embodiment(s) relate to an electro-dermal interface that supports switching between physiological measurement and information presentation to the user via associated electrodes. Information presentation is in the form of electrodermal messaging signals in different areas of the body (spatial) or intermittent signals to the skin (temporal), such as morse code, or some combination therein.

SUMMARY

A method, system, and computer program product are provided for use in an electro-dermal interface system.

In one aspect, a system is provided with a non-conductive garment, an electro-dermal interface within the garment, and a controller. The interface includes an array of electrodes to measure electro-dermal data. The electrodes are associated with three or more polarities. The interface also includes measurement circuits and switch circuitry. The measurement circuits are associated with respective measurement functions. Each of the circuits is in communication with the electrodes. The switch circuitry includes two or more pole switches. Each switch is in communication with a respective electrode. The controller is in communication with the switch circuitry and function to change the measurement function, which includes a polarity associated with at least one of the electrodes.

In another aspect, a method is provided for supporting an electrodermal interface system. The method comprising the electro-dermal interface within a non-conductive material. The interface includes an array of electrodes, two or more measurement circuits, and switch circuitry. The array of electrodes measures electro-dermal data, with the electrodes associated with three or more polarities. The measurement circuits are associated with respective measurement functions, and each of the circuits is in communication with the electrodes. The switch circuitry comprises two or more pole switches, and each switch is in communication with a respective electrode. The measurement functions are controlled with the control including changing a polarity associated with at least one of the electrodes.

In a further aspect, a computer program product is provided for supporting an electrodermal interface. The computer program product comprises a computer readable storage device having program code embodied therewith. The program code is executable by a processing unit to configure the electro-dermal interface within a non-conductive material, and to control a measurement function associated with the interface. The interface includes an array of electrodes for measuring electro-dermal data. The electrodes are associated with three or more polarities. The measurement circuits are associated with respective measurement functions. Each of the circuits is in communication with the electrodes. The switch circuitry comprises two or more pole switches, with each switch in communication with a respective electrode. The control of the measurement function includes changing a polarity associated with at least one of the electrodes.

Other features and advantages will become apparent from the following detailed description of the presently preferred embodiments, taken in conjunction with the accompanying drawings.

BRIEF DESCRIPTION OF THE SEVERAL VIEWS OF THE DRAWINGS

Through the more detailed description of some embodiments of the present disclosure in the accompanying drawings, the above and other objects, features and advantages of the present disclosure will become more apparent, wherein the same reference generally refers to the same component in the embodiments of the present disclosure.

DETAILED DESCRIPTION

Figure 1:
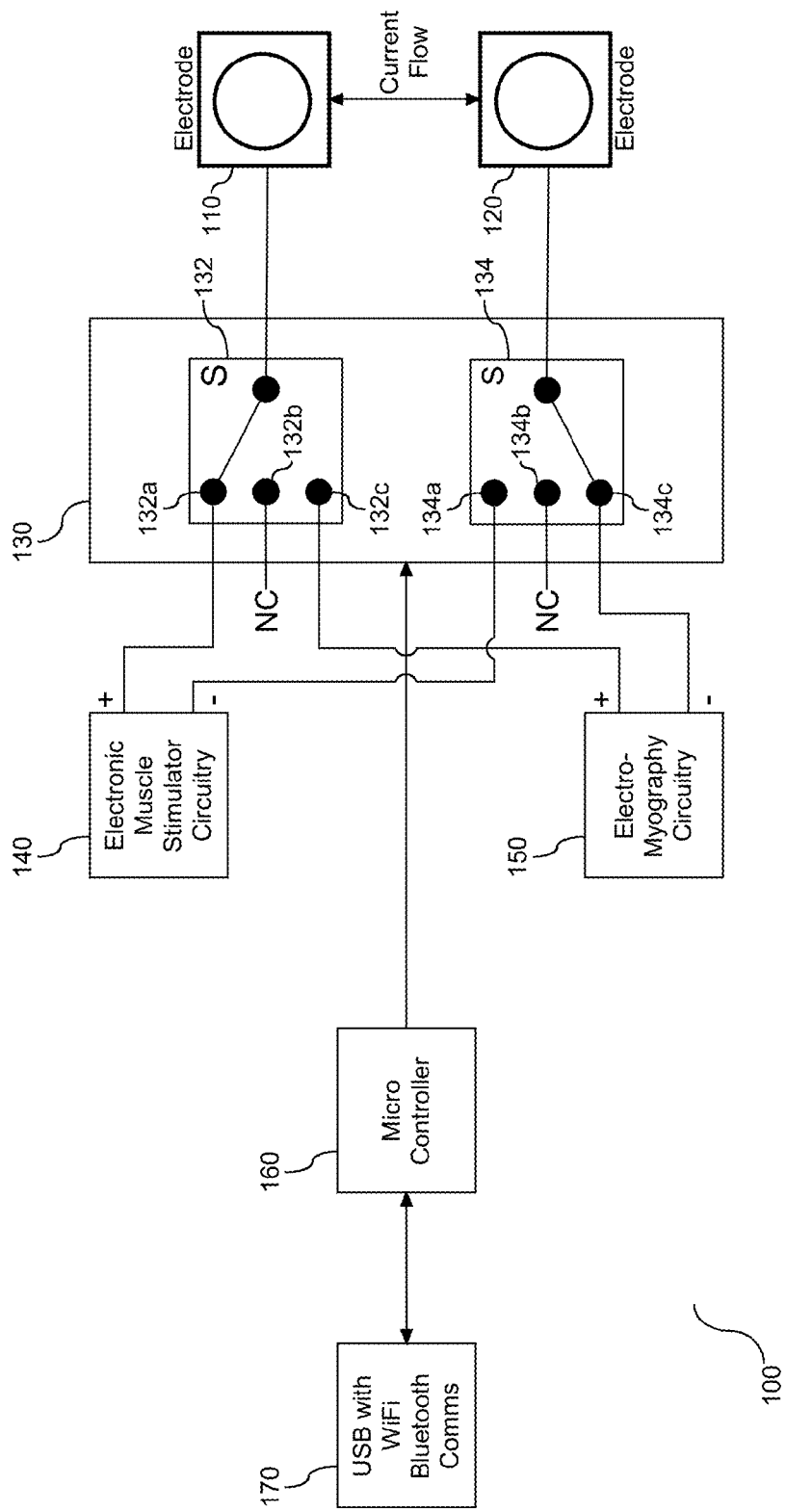
FIG. 1 depicts a block diagram illustrating an electrodermal interface with a three pole switching device.

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

As will be appreciated by one skilled in the art, aspects of the present embodiment(s) may be embodied as a system, method, or computer program product. Accordingly, aspects of the present embodiment(s) may take the form of an entirely hardware embodiment, an entirely software embodiment (including firmware, resident software, micro-code, etc.), or an embodiment combining software and hardware aspects that may all generally be referred to herein as a "circuit," "module" or "system." Furthermore, aspects of the present embodiment(s) may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present embodiment(s) may be written in any combination of one or more programming languages, including an object oriented programming language such as Java, Smalltalk, C++, or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present embodiment(s) are described below with reference to flowchart illustrations and/or block diagrams of methods, apparatus (systems), and computer program products according to the embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Physiological information describes the functions of the human body. One means to collect physiological information is through haptic collection, that is, monitoring responses to touch, such as applied forces, vibrations, or motions to a user. Alternatively, physiological information may be collected by directly monitoring or sensing electrical activity at the skin or electro-dermal activity. Active sensing includes Galvanic Skin Response(s), which comprises applying current directly to the skin to see resistance of the skin surface tissue. Passive sensing includes EMG, ECG, or EEG. Direct electrical stimulation of the skin promotes electro-dermal activity. To that end, collecting physiological information may comprise sending messaging through the skin and measuring the messaging. The messaging may occur through active monitoring, such as Galvanic Skin Response (GSR) or through passive monitoring through electromyography (EMG) and electrocardiography (ECG), the recording of the electrical activity of the heart, a diagnostic tool to assess the electrical and muscular functions of the heart (ECG or EKG). EMG and EKG both measure the electrical field created by a moving muscle. EKG is a recording of the electrical activity of the heart and measures signals from the heart muscle, yet spreads electrodes across the body. EMG places a pair of electrodes directly over a muscle to measure the muscle activity while minimizing signals from other muscles, including the heart. In one embodiment, at least one of the electrodes may be activated to stimulate a muscle in communication with the activated electrode. Similarly, with an array of electrodes, at least one of the electrodes in the array may be activated to stimulate a muscle in communication with the activated electrode. With EKG, activity is detected by electrodes attached to the surface of the skin. More than two electrodes are generally used, combined into pairs. The electrodes detect and amplify small electrical changes on the skin with each heartbeat, detected as small changes in the form of rises and falls in the voltage between two electrodes placed on either side of the heart.

Electrodes may be used to sense electrical activity or communicate electrical activity by measuring the conductivity at the surface of the skin. It is understood that the human body is not static and is constantly subject to change. Under different circumstances, the skin may have different reactions. For example, in one embodiment, the body may have a reaction that causes moisture or dampness on the skin surface in one or more select locations. To accommodate or respond to this condition, detection of moisture adjacent or proximal to one of more of the electrodes in the array may cause an adjustment of measurement of an associated electro-dermal signal. In one embodiment, the moisture detected must be in excess of a threshold value. A switch is provided that supports at least three positions, including one non-connected position. One position is negative, and another position is positive, for receipt of a signal. Any one or more of the electrodes may have the functionality switched and/or paired with other electrodes in the array.

Referring to FIG. 1, a block diagram (100) is provided illustrating an electro-dermal interface. As shown, two electrodes (110) and (120) are in communication with switching circuitry (130). Although only two electrodes (110) and (120) are shown, it is understood that additional electrodes may be employed, each in communication with the switching circuitry (130). Each electrode is configured to measure electro-dermal activity in the form of electro-dermal data. As shown, the electrode (110) is in communication with a first switch (132) embedded in the switching circuitry (130). Similarly, electrode (120) is in communication with a second switch (134) embedded in switching circuitry (130). As shown herein, both the first switch (132) and the second switch (134) are three pole switching devices. More specifically, the first switch (132) has three positions, including a first position (132a), a second position (132b), and a third position (132c). The first position (132a) completes a connection from the electrode (110) to electronic muscle stimulator circuitry (140). The second position (132b) is a neutral position in which the switch is normally closed. The third position (132c) completes a connection from the electrode (110) to electro-myography circuitry (150). Similarly, the second switch (134) has three positions, including a first position (134a), a second position (134b), and a third position (134c). The first position (134a) completes a connection from the second electrode (120) to the electronic muscle stimulator circuitry (140). The second position (134b) is a neutral position in which the switch is normally closed. The third position (134c) completes a connection from the second electrode (120) to electro-myography circuitry (150). Accordingly, the switching circuitry (130) provides an electronic interface between the electrodes (110) and (120) and both the electro-myography circuitry (150) and the electronic muscle stimulator (140).

As further shown in the interface, a micro-controller (160) is provided in communication with the switching circuitry (130). The micro-controller (160) is designed to communicate with the switching circuitry (130) in order to control functionality of the electrodes, and specifically switching and command. As further shown, the micro-controller (160) is in communication with a short range communication device (170). In one embodiment, the communication between device (170) and micro-controller (160) is bi-directional. Similarly, in one embodiment, the communication device (170) employs a wireless networking technology that uses radio waves to provide wireless high-speed Internet and network connections, also referred to herein as WiFi, or short-range radio technology among Internet devices and between devices and the Internet, also referred to herein as Bluetooth. The micro-controller (160) shown herein functions as a control system to control the switching circuitry among the electrodes in an associated array of electrodes. In one embodiment, an alternative tool may be employed as a form of a control system to control and manage the switching circuitry among the electrodes. Accordingly, the interface shown herein provides external communication with an electrode or an array of electrodes to In the embodiment shown in FIG. 1, each of the switches (132) and (134) are three pole switches, and as shown, the respective switch may be in one of three positions. As shown herein, the first electrode (110) is a positive electrode because the associated switch (132) is shown in the first position (132a) completing a connection to the electronic muscle stimulator circuitry (140). Similarly, the second electrode (120) is a negative electrode because the associated switch (134) is shown in the third position (134c) completing a connection to the electro-myography circuitry (150). In one embodiment, the polarities of the electrodes are dynamic and change with the switching circuitry. Specifically, the polarity of each of the electrodes (110) and (120) is set of the respective switch (132) and (134), respectively. The polarity of the first electrode (110) is shown as positive because the switch (132) is in the first position (132a). The polarity of the second electrode (120) is negative because the switch (134) is in the third position (134c). Accordingly, the polarity of the electrodes can change with the switching circuitry, and in one embodiment, the polarity changes dynamically.

Figure 2:
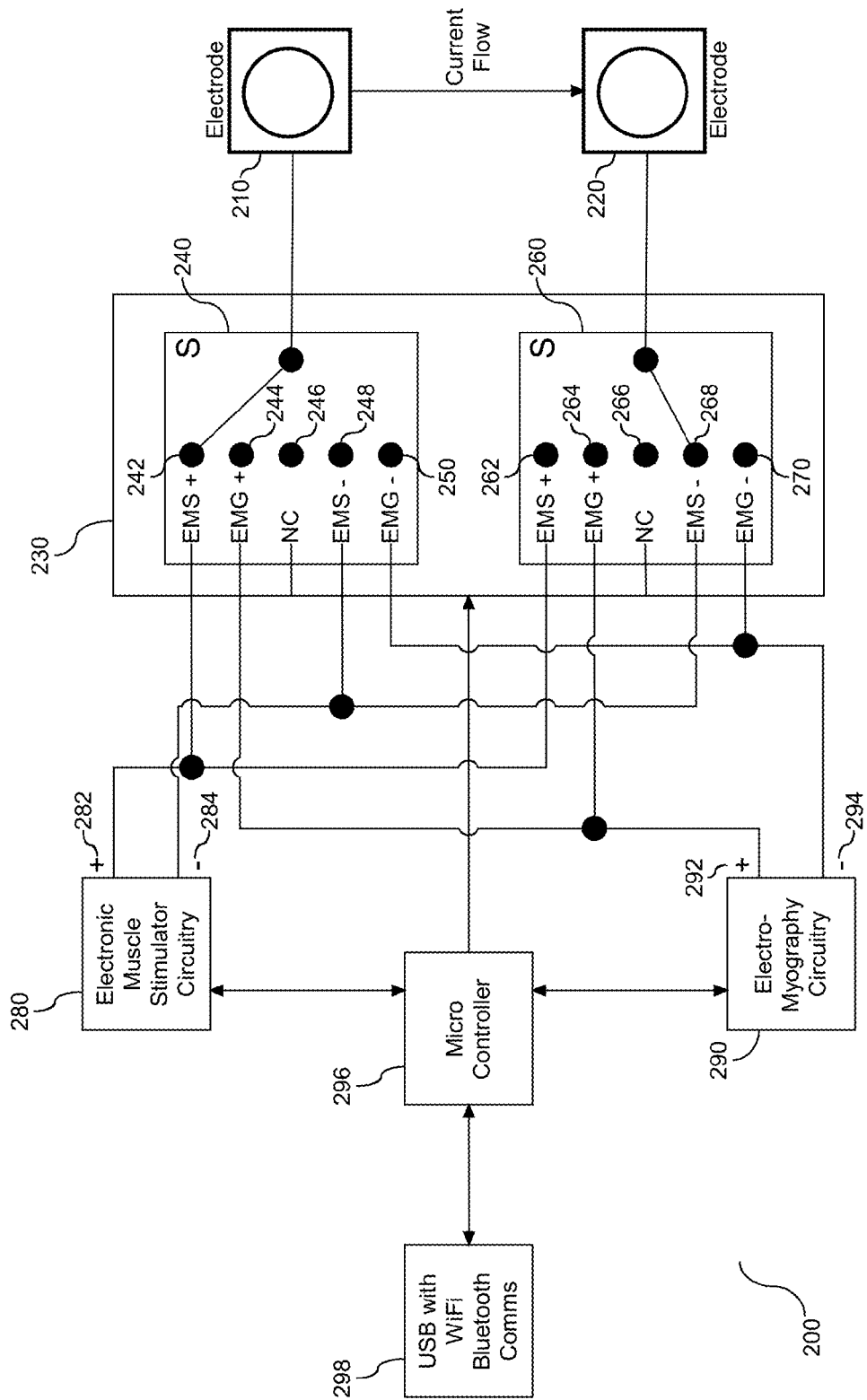
FIG. 2 depicts a block diagram illustrating an electrode an electro-dermal interface with a five pole switching device.

Referring to FIG. 2, a block diagram (200) is provided illustrating an electro-dermal interface with a five pole switching device. As shown, two electrodes (210) and (220) are in communication with switching circuitry (230). Although only two electrodes (210) and (220) are shown, it is understood that additional electrodes may be employed, each in communication with the switching circuitry (230). As shown, electrode (210) is in communication with a first switch (240) embedded in the switching circuitry (230). Similarly, electrode (220) is in communication with a second switch (260) embedded in switching circuitry (230). As shown herein, both the first switch (240) and the second switch (260) are five pole switching devices. More specifically, the first switch (240) has five positions, including a first position (242), a second position (244), a third position (246), a fourth position (248), and a fifth position (250). The first position (242) completes a positive connection from the electrode (210) to the electronic muscle stimulator (EMS) circuitry (280), and specifically, to the positive polar connection (282) of the EMS circuitry (280). The second position (244) completes a positive connection from the electrode (210) to the electro-myography (EMG) circuitry (290), and specifically, to the positive polar connection (292) of the EMG circuitry. The third position (246) is a neutral position in which the switch is normally closed. The fourth position (248) completes a connection from the electrode (210) to the EMS circuitry (280), and specifically to the negative polar connection (284). The fifth position (250) completes a connection from the electrode (210) to the EMG circuitry (290), and specifically to the negative polar connection (294). Accordingly, the polarity and associated functionality of the first electrode (210) may change based upon one of five positions in the associated switch (240).

As shown in FIG. 2, there are two electrodes. The second electrode (220) has similar switching capabilities to that shown with the first electrode (210). Electrode (220) is in communication with the second switch (260) embedded in the switching circuitry (230). As shown herein, the second switch (260) is a five pole switching device. More specifically, the second switch (260) has five positions, including a first position (262), a second position (264), a third position (266), a fourth position (268), and a fifth position (270). The first position (262) completes a positive connection from the electrode (220) to the EMS circuitry (280), and specifically, to the positive polar connection (282) of the EMS circuitry (280). The second position (264) completes a positive connection from the electrode (220) to the EMG circuitry (290), and specifically, to the positive polar connection (292) of the EMG circuitry. The third position (266) is a neutral position in which the switch is normally closed. The fourth position (268) completes a connection from the electrode (220) to the EMS circuitry (280), and specifically to the negative polar connection (284). The fifth position (270) completes a connection from the electrode (220) to the EMG circuitry (290), and specifically to the negative polar connection (294). Accordingly, the polarity and associated functionality of the second electrode (220) may change based upon one of five positions in the associated switch (260).

As further shown in the interface, a micro-controller (296) is provided in communication with the switching circuitry (230). The micro-controller (296) is designed to communicate with the switching circuitry (230) in order to control functionality of the electrodes, and specifically switching and command. As further show, the micro-controller (296) is in communication with a short range communication device (298). In one embodiment, the communication between device (298) and micro-controller (296) is bi-directional. Similarly, in one embodiment, the communication device (298) employs a wireless networking technology that uses radio waves to provide wireless high-speed Internet and network connections, also referred to herein as WiFi, or short-range radio technology among Internet devices and between devices and the Internet, also referred to herein as Bluetooth. Accordingly, the interface shown herein provides external communication with an electrode or an array of electrodes to support and enable control of functionality from a remote location.

In the embodiment shown in FIG. 1, each of the switches (132) and (134) are three pole switches, and as shown, the respective switch may be in one of three positions. The position of the switch changes the functionality of the associated electrode. Similarly, in the embodiment shown in FIG. 2, each of the switches (240) and (260) are five pole switches, and as shown, the respective switch may be in one of five positions. The polarity of the electrodes can change with the switching circuitry, and in one embodiment, the polarity changes dynamically.

Figure 3:
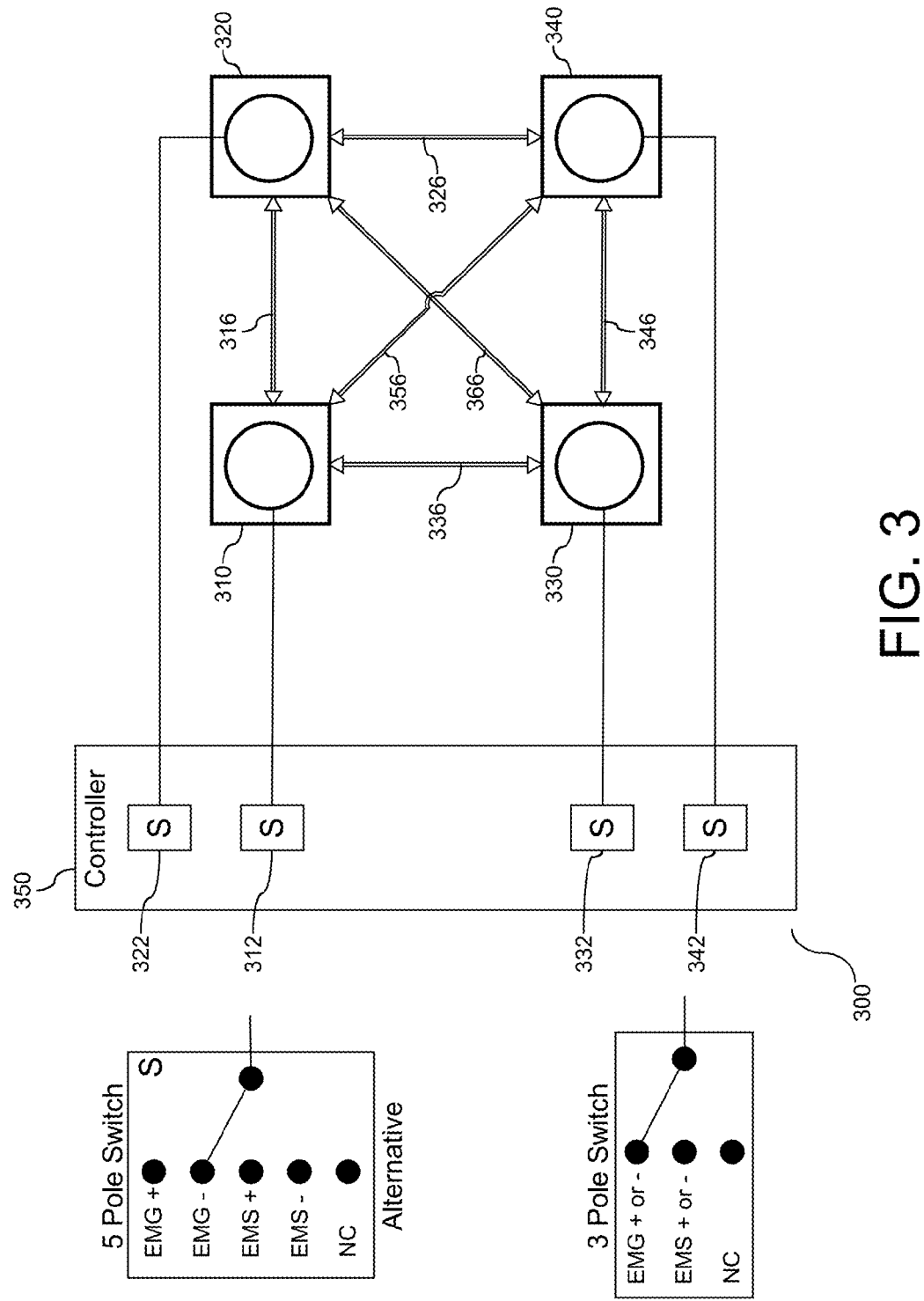
FIG. 3 depicts a block diagram illustrating an electrode pair switching system for communication.

Referring to FIG. 3, a block diagram (300) is provided illustrating an electrode pair switching system for communication. As shown herein, there are four electrodes, including $electrode_1$ (310), $electrode_2$ (320), $electrode_3$ (330), and $electrode_4$ (340). Although in one embodiment, there may be a smaller or larger quantity of electrodes in the system, and as such, the quantity shown herein should not be considered limiting. Each of the electrodes (310), (320), (330), and (340) are in communication with a controller (350) via a set of associated switches. In one embodiment, the switches are three pole switching devices as shown and described in FIG. 1, or five pole switching devices as shown and described in FIG. 2, and hereby incorporated by reference. $Electrode_1$ (310) is shown supported by switch (312), $electrode_2$ (320) is shown supported by switch (322), $electrode_3$ (330) is shown supported by switch (332), and $electrode_4$ (340) is shown supported by switch (342).

Furthermore as shown in FIG. 3, bi-directional inter-electrode communication is supported. Specifically, bi-directional communication between $electrode_1$ (310) and $electrode_3$ (330) is shown at (336). Similarly, bi-directional communication between $electrode_1$ (310) and $electrode_2$ (320) is shown at (316), bi-directional communication between $electrode_2$ (320) and $electrode_4$ (340) is shown at (326), bi-directional communication between $electrode_3$ (330) and $electrode_4$ (340) is shown at (346), bi-directional communication between $electrode_1$ (310) and $electrode_4$ (340) is shown at (356), and bi-directional communication between $electrode_3$ (330) and $electrode_2$ (320) is shown at (366). Furthermore, the electrodes shown herein (310), (320), (330), and (340) may be wired, or in one embodiment wireless, while maintaining the switching and communication functions shown herein. Accordingly, bi-directional communication is supported between each pair of electrodes in the array.

Figure 4:
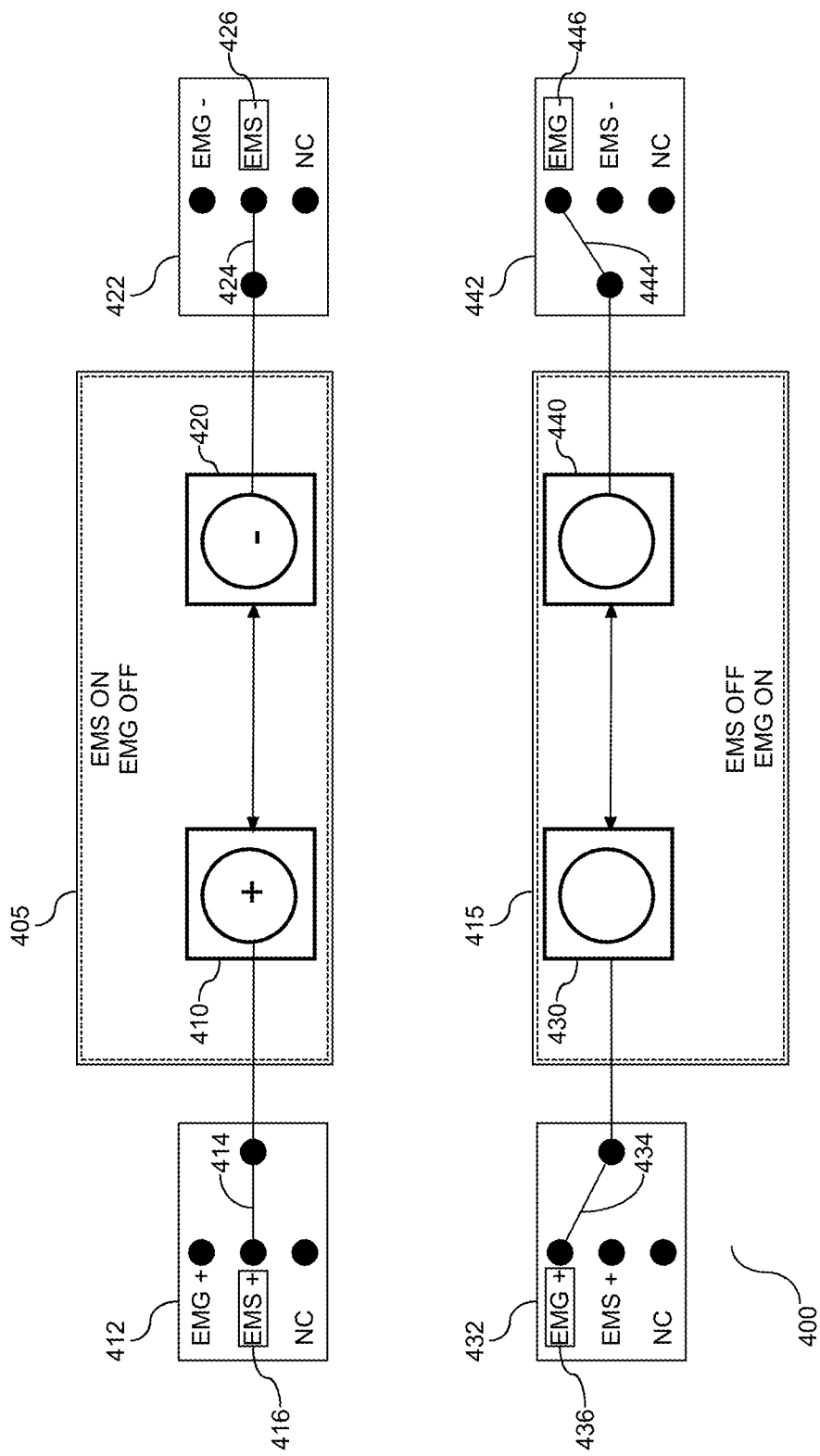
FIG. 4 depicts a block diagram of an example concurrent use of pairs of electrodes.

The system(s) shown in FIGS. 1-3, illustrate alignment and connection of electrodes with switching capabilities. The electrodes may be employed for electrical stimulation to an adjacent surface, or in one embodiment, for messaging, also referred to herein as communication. Referring to FIG. 4, a block diagram (400) of an example concurrent use of pairs of electrodes. As shown, there are two pairs of electrodes, each pair horizontally aligned. More specifically, the first pair (405) includes $electrode_0$ (410) and $electrode_1$ (420), and the second pair (415) includes $electrode_2$ (430) and $electrode_3$ (440). Each electrode is in communication with a switch. Specifically, $electrode_0$ (410) is in communication with $switch_0$ (412), $electrode_1$ (420) is in communication with $switch_1$ (422), and the second pair (415) includes $electrode_2$ (430) is in communication with $switch_2$ (432), and $electrode_3$ (440) is in communication with $switch_3$ (442). In the embodiment shown herein, $electrode_0$ (410) has a positive polarity as shown by the switch (414) connected to the positive EMS circuit (416), and $electrode_1$ (420) has a negative polarity as shown by the switch (424) connected to the negative EMS circuitry (426). As articulated above, the EMS circuit stimulates the muscle. The electrodes are limited to support messaging between the positive and negative electrodes. More specifically, the messaging support herein is from $electrode_1$ (420) to $electrode_0$ (410) to drive muscle potential, e.g. contraction or expansion. Accordingly, as shown herein in the first pair (405), the EMS messaging is ON and the EMG messaging is OFF.

As further shown herein, the second pair (415), including $electrode_2$ (430) and $electrode_3$ (440), is shown with EMS messaging OFF and EMG messaging ON. More specifically, $electrode_2$ (430) has a positive polarity as shown by the switch (434) connected to the positive EMG circuit (436), and $electrode_3$ (440) has a negative polarity as shown by the switch (444) connected to the negative EMG circuitry (446). The two horizontal pairs (405) and (415) support concurrent use with messaging between the positive electrode and the negative electrode in the pair arrangement. In one embodiment, the first pair of electrodes (405) drives muscle contraction and expansion, and the second pair of electrodes (415) drives messaging, with the muscle stimulation in the first pair extending from the second electrode, $electrode_1$ (420) to the first electrode, $electrode_0$ (410), and with messaging in the second pair (415) extending from the fourth electrode, $electrode_3$ (440) to the third electrode, $electrode_2$ (430). In one embodiment, both pairs may be employed for EMS messaging, or both pairs may be employed for EMG messaging, or in one embodiment, the EMS and EMG messaging pairs may be inverted from that shown herein. Accordingly, the horizontal alignment of the electrodes and pairing thereof supports concurrent use of both pairs of electrodes for EMS and/or EMG messaging.

Figure 5:
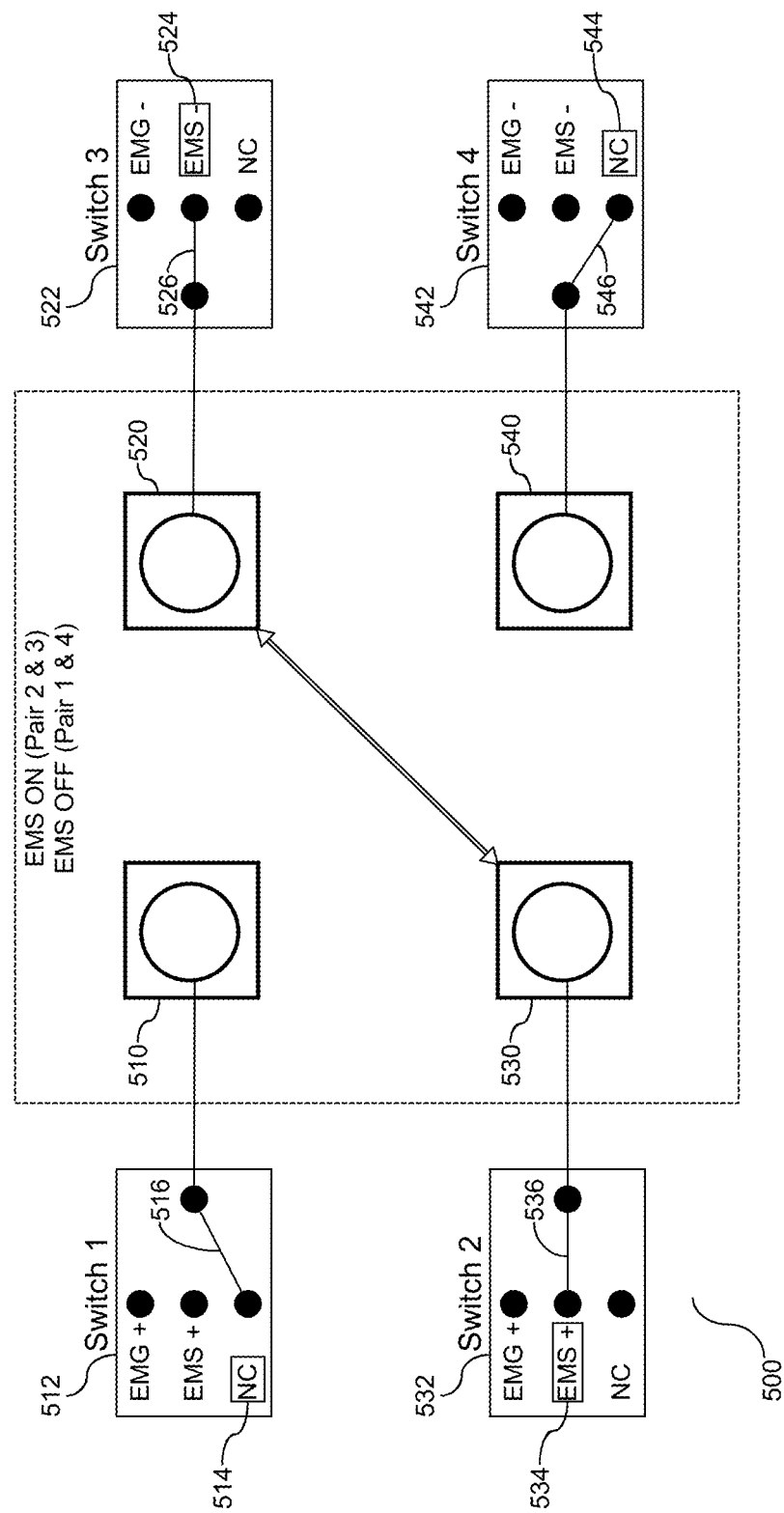
FIG. 5 depicts a block diagram of an example use of pairs of electrodes with diagonal communication between one pair of electrodes with all other combinations of electrodes off.

Referring to FIG. 5, a block diagram (500) of an example use of pairs of electrodes with diagonal communication. Similar to the configuration of FIG. 4, there are four electrodes, including electrode$_0$ (510), electrode$_1$ (520), electrode$_2$ (530), and electrode$_3$ (540). Each electrode is in communication with a switch. Specifically, electrode$_0$ (510) is in communication with switch$_0$ (512), electrode$_1$ (520) is in communication with switch$_1$ (522), electrode$_2$ (530) is in communication with switch$_2$ (532), and electrode$_3$ (540) is in communication with switch$_3$ (542). In the embodiment shown herein, electrode$_0$ (510) is not connected (514) as shown at (516) by the switch (512) and electrode$_3$ (540) is also not connected (544) as shown at (546) with the switch (546). Electrode$_1$ (520) is in communication with electrode$_2$ (530). More specifically, electrode$_1$ (520) has a negative polarity as shown at (526) with the switch (522) connected to the negative EMS circuitry (524), and electrode$_2$ (530) has a positive polarity (534) as shown at (536) with the switch (532). As articulated above, the EMS circuit stimulates the muscle. The electrodes are limited to support messaging between the positive and negative electrodes. More specifically, the messaging support herein is from electrode$_1$ (520) to electrode$_3$ (530) to drive muscle contraction or expansion. Accordingly, as shown in the example herein, the first and fourth electrodes (510) and (540), respectively, are not connected, and communication is supported diagonally across the array between the second and third electrodes (520) and (530) to support EMS messaging there between.

As shown in FIG. 5, there are various combinations of electrodes, and the pairings are not limited to a one to one relationship. In the example shown herein, any one of the electrodes (510), (520), (530), and (540) could be communicating with one, two, or three other electrodes in the array. For example, based on the array shown herein, the electrodes can have a 1:1 relationship, a 1:2 relationship, or a 1:3 relationship, with one switch being positive, and the other switches being negative or grounded. An example of a 1:1 relationship is with electrode$_0$ (510) in communication with electrode$_1$ (520), electrode$_0$ (510) in communication with electrode$_2$ (530), and electrode$_0$ (510) in communication with electrode$_3$ (540). An example of a 1:2 relationship is with electrode$_0$ (510) in communication with electrode$_1$ (520) and electrode$_2$ (530), and electrode$_0$ (510) in communication with and electrode$_2$ (530) and electrode$_3$ (540). Similarly, an example of a 1:3 relationship is with electrode$_0$ (510) in communication with electrode$_1$ (520), electrode$_2$ (530), and electrode$_3$ (540). In an embodiment with a larger array, the combination of communications among electrodes may be expanded to include every electrode in the array.

Figure 6:
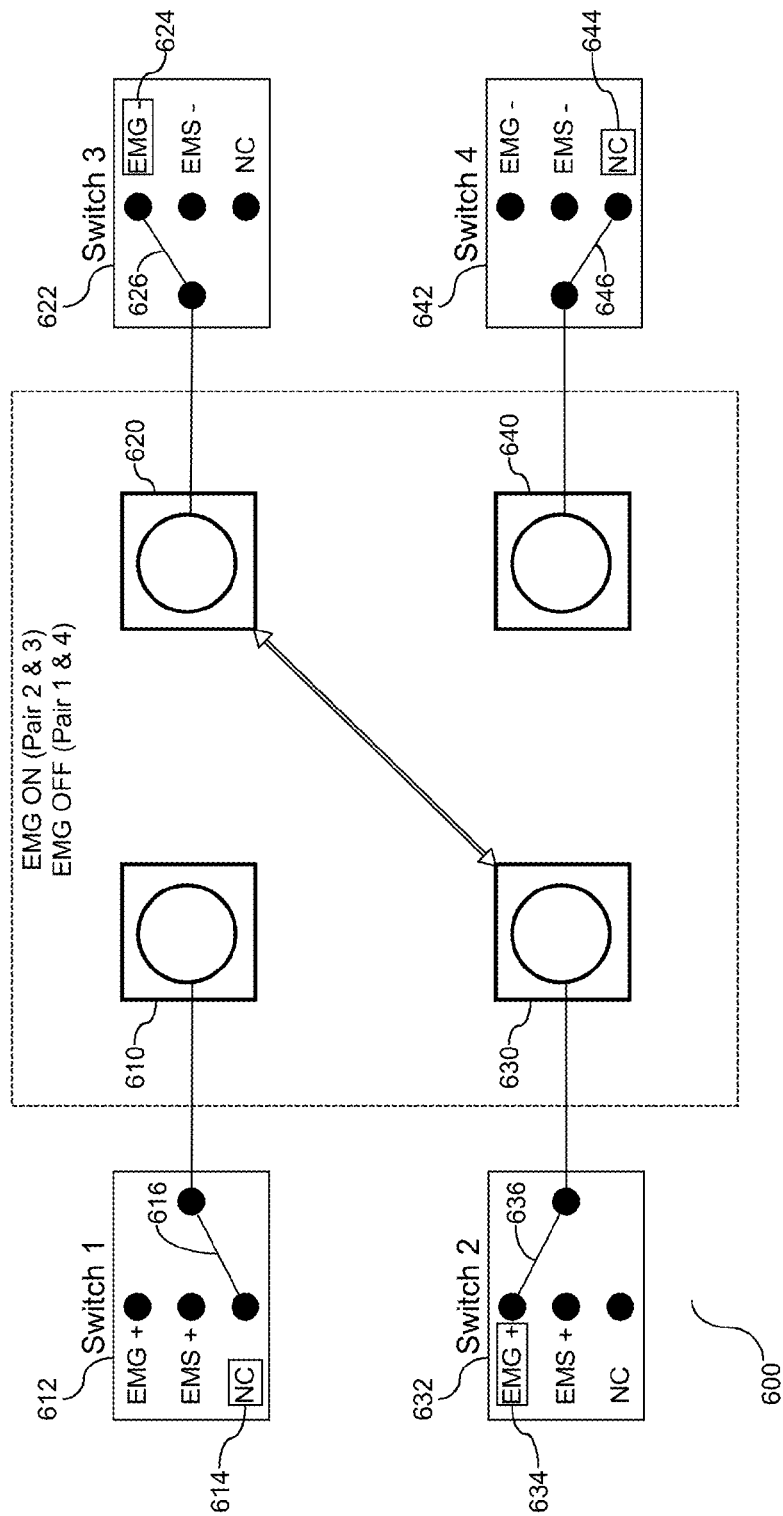
FIG. 6 depicts a block diagram of an example use of pairs of electrodes with diagonal communication for EMG messaging between one pair of electrodes with all other combinations of electrodes off.

Referring to FIG. 6, a block diagram (600) of an example use of pairs of electrodes with diagonal communication for EMG messaging. Similar to the configuration and functionality of FIG. 5, there are four electrodes, including electrode$_0$ (610), electrode$_1$ (620), electrode$_2$ (630), and electrode$_3$ (640). Each electrode is in communication with a switch. Specifically, electrode$_0$ (610) is in communication with switch$_0$ (612), electrode$_1$ (620) is in communication with switch$_1$ (622), electrode$_2$ (630) is in communication with switch$_2$ (632), and electrode$_3$ (640) is in communication with switch$_3$ (642). In the embodiment shown herein, electrode$_0$ (610) is not connected (614) as shown by the switch (616) and electrode$_3$ (640) is also not connected (644) as shown by the switch (646). Electrode$_1$ (620) is in communication with electrode$_2$ (630). More specifically, electrode$_1$ (620) has a negative polarity as shown by the switch (622) connected to the negative EMG circuitry (624) by switch (626), and electrode$_2$ (630) has a positive polarity as shown by the switch (636) connected to the positive EMG circuitry (634). As articulated above, the EMG circuit measures electrical activity of the heart. The electrodes are limited to support messaging between the positive and negative electrodes. More specifically, the messaging support herein is from electrode$_1$ (620) to electrode$_3$ (630) to drive electrical stimulation. Accordingly, as shown in the example herein, the first and fourth electrodes (610) and (640), respectively, are not connected, and communication is supported diagonally across the array between the second and third electrodes (620) and (630) to support EMG sensing therebetween.

Figure 7:
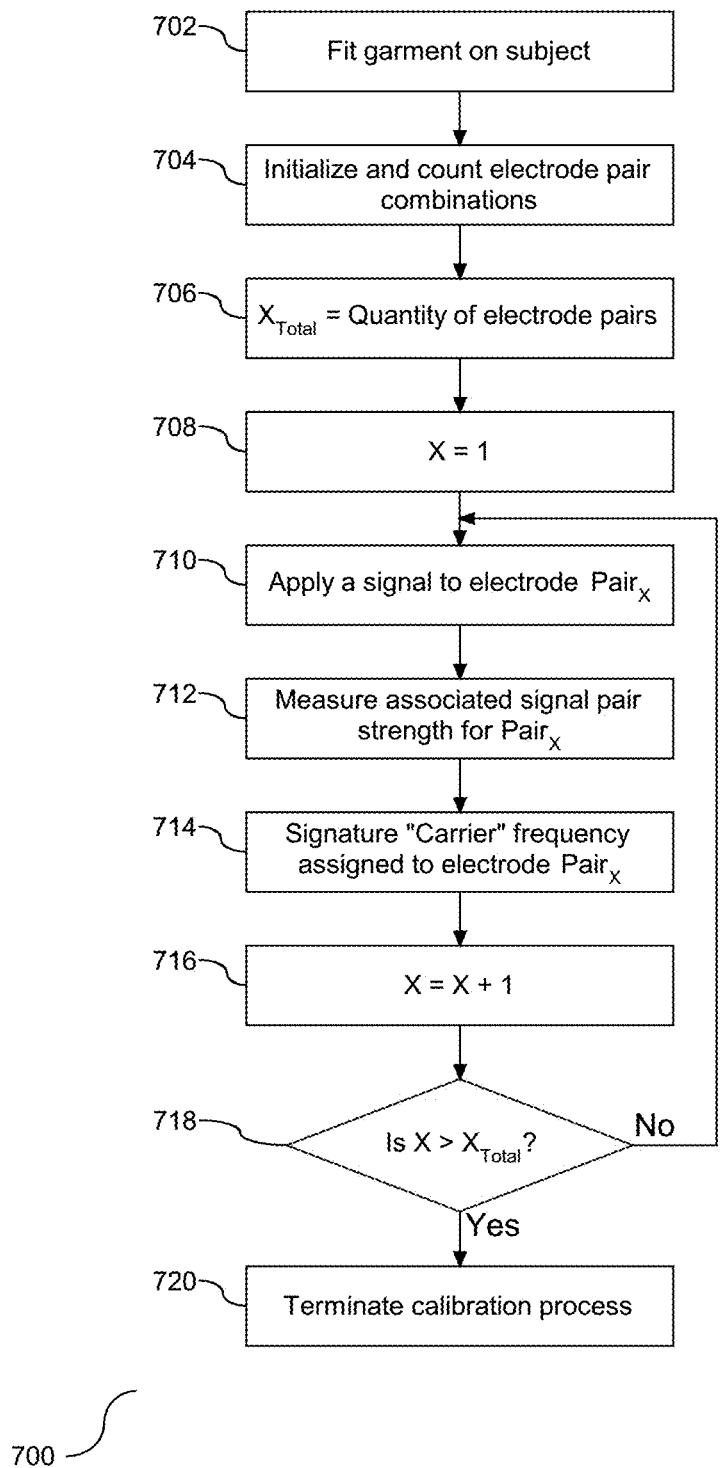
FIG. 7 depicts a flow chart illustrating a process for calibrating the array of electrodes.

As articulated above, an array of electrodes is provided to support messaging and stimulation. Referring to FIG. 7, a flow chart (700) is provided illustrating a process for calibrating the array of electrodes. In one embodiment, the electrodes and that associated electro-dermal interface are embedded in a garment, which when worn, enables the electrodes to be placed in close proximity to select body parts to support EMG, EMS, and galvanic skin response.

A garment may be used to embed the electrodes. Specifically, the electrodes may be embedded in, for instance, a t-shirt or undergarment(s) in conjunction with a conductive patch. The garments are not conductive although they comprise a conductive patch. Electrodes in the outer garment approximately line up with the patches to transmit the electrical signal from the electrodes. The surface of the garment impacts how approximately the electrodes in the outer garment align with the patches in the under garment. The alignment maximizes contact density in areas, that is, the number of contacts per square inch. In one embodiment, the undergarment is machine washable. In one embodiment, the apparatus described herein above is low power and low weight, embedded within a special undershirt. Alternatively, the apparatus is embedded in an outer garment in conjunction with an undergarment with a conductive patch. The undergarment is non-conductive or comprised of a non-conductive material except for the conductive material patches. The electrodes in the outer garment lines up with the patches to transmit the signals. The alignment may be less than an exact alignment based on the surface area of the garments. Regardless, the apparatus attempts to align the outer garment with the patches to maximize contact density in those areas. In an embodiment, the contacts per square inch are determined.

As shown, the garment is fitted to the subject (702). Messaging takes place between pairs of electrodes. As such, each electrode pair is assigned a signature. Electrode pair combinations are counted and initialized (704). The variable $X_{Total}$ is assigned to the quantity of electrode combination pairs (706), and an associated counting variable is initialized (708). A signal is applied to electrode pair$_X$ (710). Thereafter, the associated signal pair strength is measured for pair$_X$ (712), and a signature carrier frequency is assigned to the electrode pair$_X$ (714). Following the assignment at step (714), the electrode pair counting variable is incremented (716). It is then determined if all of the electrode pairs have been assigned a signature frequency (718). A negative response to the determination at step (718) is followed by a return to step (710). However, a positive response to the determination at step (718) terminates the electrode pair calibration process (720).

Figure 8:
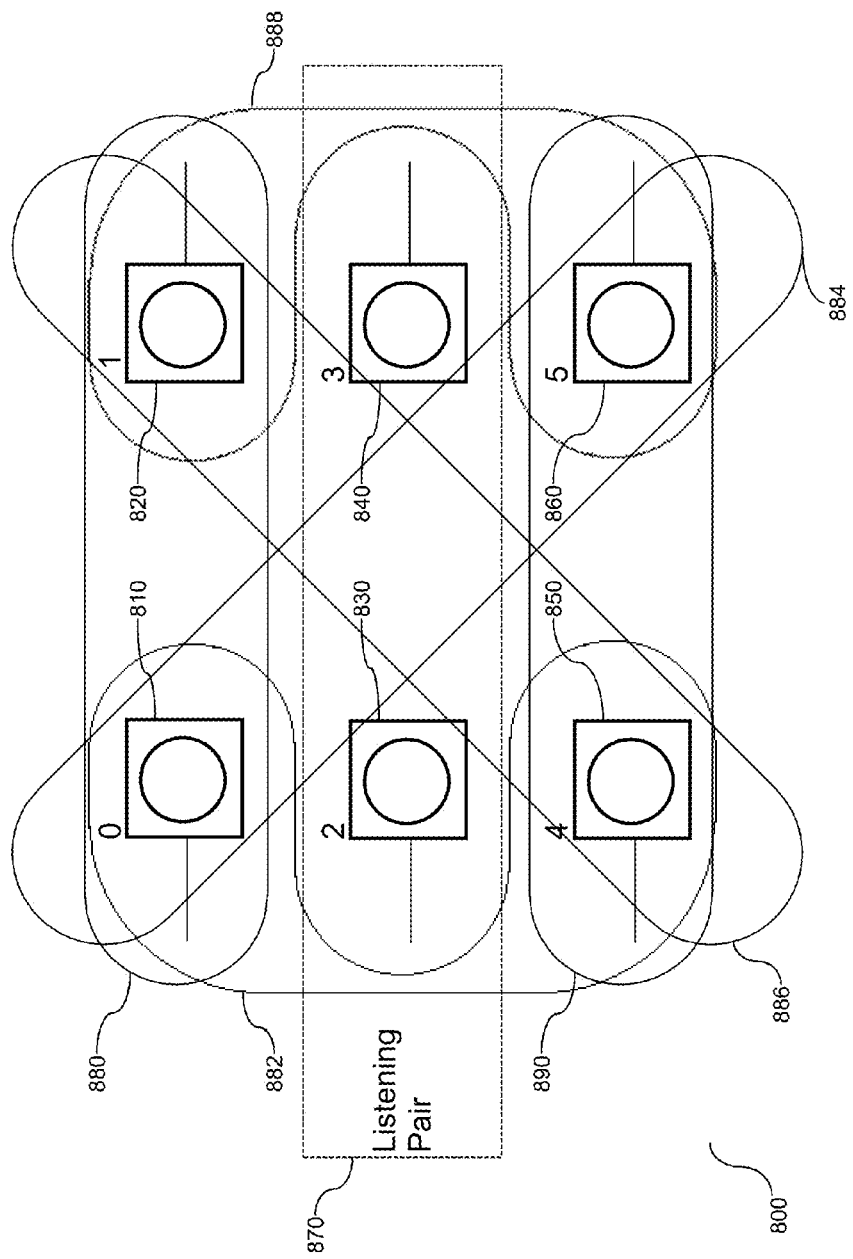
FIG. 8 depicts a block diagram demonstrating an example of noise calibration in an array of electrodes.

As shown in FIG. 7, each pair of electrodes in the array is assigned a signal with an embedded signature. It is important to mitigate noise between the different electrode pairs. For any pair of electrodes in the array, of which there are multiple pairings, noise evaluation is conducted. Referring to FIG. 8, a block diagram (800) is provided demonstrating an example of noise calibration in an array of electrodes. As shown, there are six electrodes in the array, including $electrode_0$ (810), $electrode_1$ (820), $electrode_2$ (830), $electrode_3$ (840), $electrode_4$ (850), and $electrode_5$ (860). For purposes of description, $electrode_2$ (830) and $electrode_3$ (840) form a listening pair (870) in this example. The signal of the listening pair (870) is compared to all other pairs or possible pairings of electrodes. In the example array, there are six pairings of electrodes in addition to the listening pair (870). The pairings include a first pair (880) of $electrode_0$ (810) and $electrode_1$ (820), a second pair (882) of $electrode_0$ (810) and $electrode_4$ (850), a third pair (884) of $electrode_0$ (810) and $electrode_5$ (860), a fourth pair (886) of $electrode_1$ (820) and $electrode_4$ (850), a fifth pair (888) of $electrode_1$ (820) and $electrode_5$ (860), and a sixth pair (890) of $electrode_4$ (850) and $electrode_5$ (860). The listening pair (870) is calibrated by listening for signature noise from all other combinations of electrode pairs (880)-(890). The calibration shown in this example is a form of initial pairing calibration. In one embodiment, the calibration shown herein can be expanded to a one to many or many to one electrode pairing.

As shown and described above with respect to FIG. 7, each pair of electrodes is assigned a signature signal. In one embodiment, each pair is assigned a signature EMS signal separate from assignment of an EMG signal. Similarly, in one embodiment, each pair is assigned a base signal in the frequency range of 80-100 Hz. Similarly, in one embodiment, a modulated high frequency carrier signal identifies signaling electrodes, and the frequency varies for each electrode, thereby providing a unique signature to each electrode pair.

The electrodes shown in the embodiments of FIGS. 1-3 may come in different forms to sense and communicate with various forms of data. For example, in one embodiment, one or more of the electrodes in the array may be in the form of an electro-dermal electrode to measure resistance of adjacent tissue to current. In one embodiment, the measured resistance may be compared to a threshold value, and if the resistance exceeds this value one or more electrodes that are proximal to the measured resistance may be disable, and at the same time a message associated with the measured resistance may be re-routed. Furthermore, the electrodes shown in FIG. 3 are mounted on or within a garment, which may include any form of garment, including, but not limited to, an undergarment and an outer-garment. Regardless of the form of the garment, the electrodes are mapped to the subject, so that different electrodes are mapped to specific areas of the body of the subject.

Similarly, the electrodes support simultaneous communication between different pairs. For example, one set of circuits may measure and drive two electrode pairs simultaneously. The switches described above allow both driving and monitoring at the same time. For example, one pair of electrodes within the array may be signaling at the same time as another pair of electrodes may be reading a signal. Similarly, one pair of electrodes in the array may be configured to EMS circuitry at the same time as another pair in the array is configured for EMG circuitry. The two forms of circuitry are not mutually exclusive.

As shown in FIGS. 7 and 8, the calibration process includes testing signal strength to each electrode pair in the array, which may be employed for both mapping and de-confliction purposes. With the electrodes in an array arrangement it is critical that any interference between electrodes be minimized so that appropriate signals are communicated to the proper electrode or mapping of electrodes. In one embodiment, the interference between signals may occur if the electrodes are positioned within close proximity. The interference in the signals may be identified by proper encoding of the signal, e.g. can differentiate between detected signals. In one embodiment, the de-confliction is referred to as spatial de-confliction, with electrode data from a first electrode in the array at a first location messaging data to a second electrode in the array at a second location, wherein the electrodes are spaced apart to mitigate interference.

Figure 9:
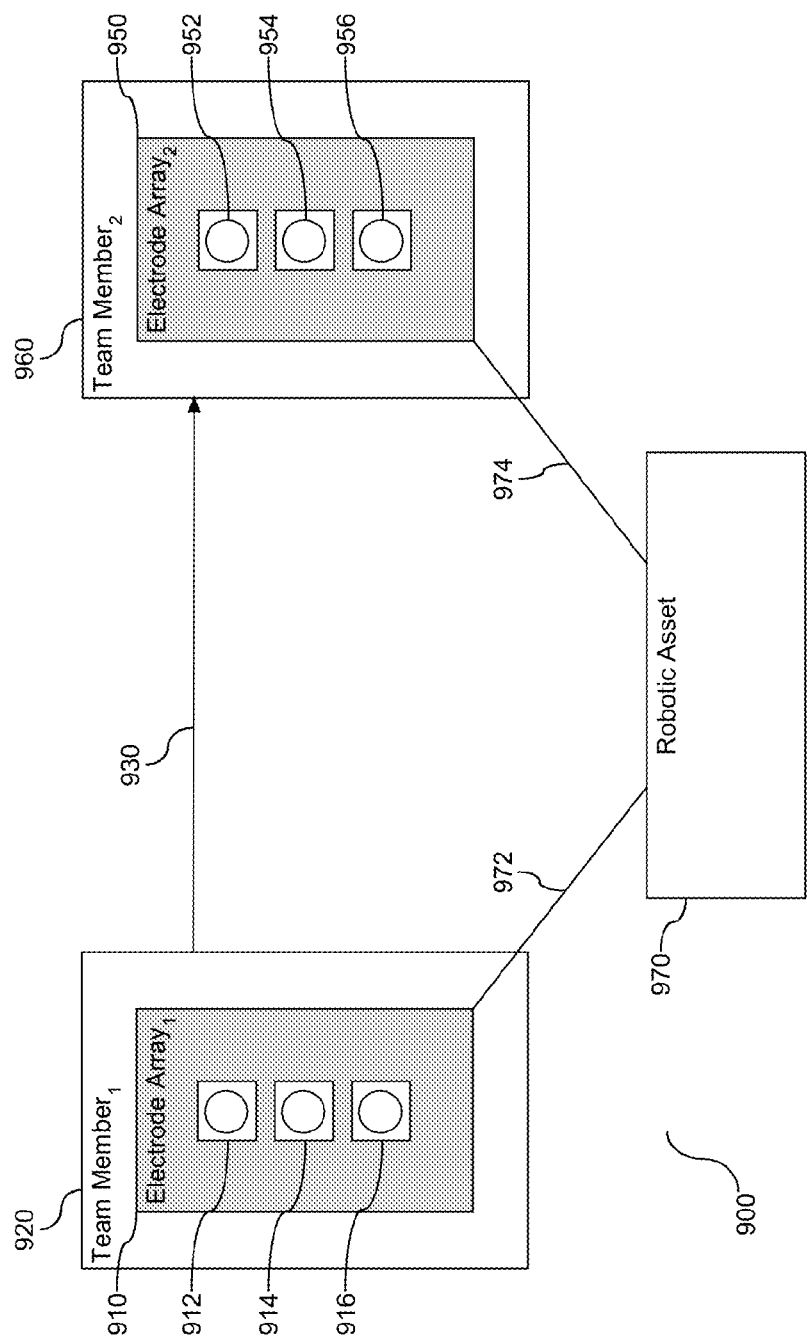
FIG. 9 depicts a block diagram illustrating multiple arrays of electrodes.

The interference assessment and re-assignment shown and described above is for a single electrode array. In one embodiment, there may be multiple arrays of electrodes that are employed as a communication tool. For example, a first array may be in communication with a first entity, and a second array may be in communication with a second entity. Referring to FIG. 9, a block diagram (900) is provided illustrating multiple arrays of electrodes. As shown, there are two arrays of electrodes, including a first array (910) and a second array (950). The first array (910) is shown local to a first member (920), and the second array (950) is shown local to a second team member (960). More specifically, the first array (910) is shown with three electrodes (912), (914), and (916), and the second array (950) is shown with three electrodes (952), (954), and (956). However, the quantity of electrodes in each array (910) and (950) should not be considered limiting. The first and second electrode arrays (910) and (950), respectively, form a team. In one embodiment, the team may be expanded to include additional members.

The electrode arrays and associated signals there between may serve as a communication interface between the entities, also referred to herein as team members. In one embodiment, the one or more of the electrodes (912) of the first entity may sense an increase in heart rate of the first entity, and this sensed increase is communicated (930) to the second entity (950). In one embodiment, the increased heart rate may be transmitted as a signal to an electrode of the second team member (950). The team may be expanded to include a robotic asset (970). As shown, the robotic asset (970) is in communication with both the first array (910) and the second array (950) at (972) and (974), respectively. The robotic asset (970) is configured to both send one or more signals to the team members, and to receive one or more signals from the team members. More specifically, the communication with the robotic asset may be to one or more specific electrodes in the team. In one embodiment, the electrodes are separately addressable. Similarly, in one embodiment, an interference assessment may be conducted between each array in the system, similar to the assessment shown and described in FIG. 8 but expanded to the respective arrays in the system. The interference assessment between or among arrays mitigates signal interference among electrodes within a single array, and among electrodes between two or more arrays.

The array of electrodes shown and described herein is not limited to a single garment. Furthermore, the electrodes are not limited by a wired connection. In one embodiment, the electrodes may be wireless. Similarly, in one embodiment, a select set of electrodes may have a wired connection, while one or more electrodes may be in a wireless connection with the array. Furthermore, the electrodes shown and described in FIGS. 1-5 pertain to measurement of resistance of adjacent tissue. However, other forms of electrodes should not be excluded. In one embodiment, the electrode may sense heart rate, and employ the sensed heart rate with the electrode array. In one embodiment, a baseline heart rate may be attained, so that the sensing of the heart rate may include variability of the heart rate as compared to the baseline.

Similarly, in one embodiment, the electrodes may be configured for sensitivity, including sensing an increased heart rate with minimal activity.

The flowcharts and block diagrams in the Figures illustrate the architecture, functionality, and operation of possible implementations of systems, methods, and computer program products according to the various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustrations, can be implemented by special purpose hardware-based systems that perform the specified functions or acts, or combinations of special purpose hardware and computer instructions.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application, or technical improvement over technologies found in the marketplace, or to enable others of ordinary skill in the art to understand the embodiments disclosed herein.

It will be appreciated that, although specific embodiments have been described herein for purposes of illustration, various modifications may be made without departing from the spirit and scope of the embodiment(s). In particular, in one embodiment, a message is encoded into an array of electrodes in the form of an electrical pattern, voltage variations, feel pulses, etc. Encoding identifies interferences in signals. As a result, encoding provides for differentiating between detected signals. In one embodiment, the apparatus, as described herein above, can be used to detect wounds because it can detect bleeding. Further, the apparatus can detect shock from muscular shaking. In another embodiment, voice signals are transmitted as messages to the electro-dermal apparatus. Alternatively, hand signals may be transmitted as messages to the electro-dermal apparatus. Command and control communications receive the signals and, in response, forward medical status communications. In another embodiment, the information presentation messages may be a power warning, such as "low power" or a spatial directional cue in the azimuth to a hostile threat. Accordingly, the scope of the embodiment(s) is limited only by the following claims.

What is claimed is:

1. A system comprising:
   a garment comprising a non-conductive material;
   an electro-dermal interface comprised within the garment, the electro-dermal interface comprising:
      a first array of electrodes to measure electro-dermal data, the first array configured with a first electrode pair including a first electrode and a second electrode, each electrode having a single polarity, including the first electrode having a first polarity and the second electrode having a second polarity, and the first electrode having a first centroid positioned at a first position and the second electrode having a second centroid positioned at a second position;
      a first circuit having a first function and a second circuit having a second function, the first and second functions selected from the group consisting of:
      measurement and stimulation, and the first and second circuits in communication with the first array of electrodes, wherein the first and second functions are different; and
      switch circuitry comprising two or more pole switches, wherein each switch is in communication with a respective electrode;
   a controller in communication with the switch circuitry to change a polarity setting associated with at least one of the first and second electrodes, wherein the polarity change dynamically creates a dependent pair relationship between the first and second electrodes, wherein the first and second electrodes are in communication with a single one of the first and second circuits; and
   the electro-dermal interface configured to perform spatial de-confliction, including receiving electrode data from the first and the second electrode in the first array at a first location and messaging data to a third and a fourth electrode in the first array at a second location, wherein the electrodes are spaced apart to mitigate interference.

2. The system of claim 1, wherein paired electrodes are in bi-directional communication.

3. The system of claim 1, wherein the first array of electrodes is configured to measure heart rate data.

4. The system of claim 1, wherein one of the circuits is an electronic muscle stimulator (EMS) circuit for muscle stimulation and one of the circuits is an electromyography (EMG) circuit to measure muscle activity.

5. The system of claim 4, further comprising an electro-dermal information presentation message including stimulation by two or more electrodes in the first array.

6. The system of claim 4, wherein at least one of the pole switches has at least three positions, including a first position to complete a connection from the respective electrode to the EMS circuit, a second position being a neutral position, and a third position to complete a connection from the respective electrode to the EMG circuit.

7. The system of claim 6, wherein the first position is a positive polarity position and the third position is a negative polarity position.

8. The system of claim 4, wherein at least one of the pole switches has at least five positions, including a first position to complete a first connection from the respective electrode to the EMS circuit, a second position to complete a second connection from the respective electrode to the EMG circuit, a third position being a neutral position, a fourth position to complete a third connection from the respective electrode to the EMS circuit, and a fifth position to complete a fourth connection from the respective electrode to the EMG circuit.

9. The system of claim 8, wherein the first and second positions are positive polarity positions and the fourth and fifth positions are negative polarity positions.

10. The system of claim 1, further comprising the electro-dermal interface configured to perform identification of interference in detected signals, including, an encoded message transmitted from one of the electrodes in the first array of electrodes through a dermal layer and received by another electrode in the first array of electrodes to differentiate between the detected signals from different electrodes.

11. The system of claim 10, wherein the encoded message is encoded in a form selected from the group consisting of: an electrical pattern, voltage variations, and any combination thereof.

12. The system of claim 1, further comprising the electro-dermal interface configured to measure electrical resistance proximal to an electrode of the first array and in response to the measured resistance exceeding a threshold, the electro-dermal interface to disable the electrode and to re-route messaging to a different electrode of the first array.

13. The system of claim 1, further comprising the electro-dermal interface configured to measure moisture proximal to an electrode of the first array and in response to the measured moisture exceeding a threshold, the electro-dermal interface to adjust the measured electro-dermal data.

14. The system of claim 1, further comprising:
a team having at least two members, the team comprising:
  a first member having the first array of electrodes;
  a second member having a second array of electrodes, the second array configured with a second electrode pair including a set of electrodes, each electrode in the set having a single polarity, including the one of the electrodes in the set having the first polarity and the one of the electrodes in the set having the second polarity, the electrodes in the set are in communication with two or more additional circuits, each electrode in the set is in communication with a respective second switch; and
  a robotic asset in communication with the first and second arrays, the robotic asset configured to communicate with the team, including the robotic asset to send a signal to at least one of the arrays and receive a signal from at least one of the arrays, wherein the electrodes in the first and second arrays are separately addressable.

15. The system of claim 14, further comprising the first array configured to attain a baseline heart rate, and to measure heart rate variability, including the first array to sense a condition of a first entity selected from the group consisting of: a change in the heart rate and a change in heart rate variability.

16. The system of claim 15, further comprising the robotic asset configured to receive the sensed condition as a communication and configured to send a signal to the second array wherein at least one electrode of the second array transmits an encoded message.

17. The system of claim 16, wherein the encoded message is converted into an electro-dermal coding selected from the group consisting of: temporal message, spatial message, a feel variation, a feel pulse, force feedback message, and morse code.

18. The system of claim 1, further comprising the polarity change creating a communication channel between the first and second electrodes, wherein the communication channel transmits a voltage potential between the first and second electrodes.

19. A system comprising:
a team having at least two members and a robotic asset, wherein the robotic asset is configured in communication with each member, wherein each member of the team comprises:
  an electro-dermal interface comprising:
    an array of electrodes to measure electro-dermal data, wherein each electrode is associated with one of at least two polarities, wherein each electrode is independently positionable;
    two or more circuits associated with a function selected from the group consisting of: measurement, stimulation, and messaging, each of the circuits in communication with the array of electrodes, including a first circuit with a first function and a second circuit with a second function, wherein the first and second functions are different; and
    switch circuitry comprising two or more pole switches, wherein each switch is in communication with a respective electrode and one or more of the circuits; and
    a controller in communication with the switch circuitry to change a polarity associated with at least one of the electrodes;
  each member of the team in communication with a separate entity; and
  the robotic asset configured to receive a sensed condition from a first member and to send the sensed condition as a signal to a second array of electrodes wherein at least one electrode of the second array of electrodes transmits an encoded message, wherein the encoded message is converted into an electro-dermal coding selected from the group consisting of: temporal message, spatial message, a feel variation, a feel pulse, force feedback message, and morse code.

20. A system comprising:
a team having at least two members and a robotic asset, wherein the robotic asset is configured in communication with each member, wherein each member of the team comprises:
  an electro-dermal interface comprising:
    an array of electrodes to measure electro-dermal data, wherein each electrode is associated with one of at least two polarities, wherein each electrode is independently positionable;
    two or more circuits associated with a function selected from the group consisting of: measurement, stimulation, and messaging, each of the circuits in communication with the array of electrodes, including a first circuit with a first function and a second circuit with a second function, wherein the first and second functions are different; and
    switch circuitry comprising two or more pole switches, wherein each switch is in communication with a respective electrode and one or more of the circuits; and
    a controller in communication with the switch circuitry to change a polarity associated with at least one of the electrodes;
  each member of the team in communication with a separate entity; and
  the robotic asset configured to receive a sensed condition from a first member and to send a signal to a second array of electrodes wherein at least one electrode of the second array of electrodes transmits an encoded message, wherein the encoded message is converted into an electro-dermal coding.

21. A system comprising:
a garment comprising a non-conductive material;
an electro-dermal interface comprised within the garment, the electro-dermal interface comprising:
  a first array of electrodes to measure electro-dermal data, the first array configured with a first electrode pair including a first electrode and a second electrode, each electrode having a single polarity, including the first electrode having a first polarity and the second electrode having a second polarity, and the first electrode having a first centroid positioned at a first location and the second electrode having a second centroid positioned at a second location;

a first circuit having a first function and a second circuit having a second function, the first and second functions selected from the group consisting of: measurement and stimulation, and the first and second circuits in communication with the first array of electrodes, wherein the first and second functions are different; and switch circuitry comprising two or more pole switches, wherein each switch is in communication with a respective electrode;

a controller in communication with the switch circuitry to change a polarity setting associated with at least one of the first and second electrodes, wherein the polarity change dynamically creates a dependent pair relationship between the first and second electrodes, wherein the first and second electrodes are in communication with a single one of the first and second circuits; and the electro-dermal interface configured to perform identification of interference in detected signals, including, an encoded message transmitted from the first electrode in the first array of electrodes through a dermal layer and received by the second electrode in the first array of electrodes to differentiate between the detected signals from different electrodes.

* * * * *